United States Patent [19]

Drozd et al.

[11] Patent Number: 4,668,423

[45] Date of Patent: May 26, 1987

[54] LIQUID BIODEGRADABLE SURFACTANT AND USE THEREOF

[75] Inventors: Joseph C. Drozd, Park Ridge, Ill.; Richard R. Egan, Worthington, Ohio

[73] Assignees: Sherex Chemical Company, Dublin, Ohio; Stepan Company, Northfield, Ill.

[21] Appl. No.: 725,281

[22] Filed: Apr. 19, 1985

[51] Int. Cl.$^4$ ...................... C07C 41/03; C07C 43/15; C11D 1/722; C11D 1/831

[52] U.S. Cl. ............................... 252/174.21; 252/153; 252/173; 252/540; 252/548; 252/559; 252/DIG. 1; 252/DIG. 14; 568/616; 568/625

[58] Field of Search ............ 252/174.21, 173, DIG. 1, 252/135, 99; 568/616, 625

[56] References Cited

U.S. PATENT DOCUMENTS

| | | | |
|---|---|---|---|
| 3,504,041 | 3/1970 | Weipert | 260/615 |
| 3,507,798 | 4/1970 | Egan | 252/135 |
| 3,567,784 | 3/1971 | Tsatsos | 252/174.21 |
| 3,770,701 | 11/1973 | Cenker | 252/174.21 |
| 3,969,134 | 7/1976 | Batka | 252/174.21 |
| 4,207,421 | 6/1980 | Scardera | 568/625 |
| 4,280,919 | 7/1981 | Stoeckigt | 252/135 |

FOREIGN PATENT DOCUMENTS

| | | | |
|---|---|---|---|
| 2810703 | 9/1978 | Fed. Rep. of Germany | 568/625 |
| 922252 | 3/1963 | United Kingdom | 568/625 |
| 1601652 | 11/1981 | United Kingdom | 568/625 |

*Primary Examiner*—Dennis L. Albrecht

*Attorney, Agent, or Firm*—Pollock, Vande Sande & Priddy

[57] ABSTRACT

Liquid biodegradable surfactant having oxyethylene and oxypropylene groups attached to the residue of an alcohol having a minimum iodine value of at least 40 wherein the ratio of oxyethylene groups to oxypropylene groups is at least 4:1, and the total moles of oxyethylene and oxypropylene groups is about 9 to about 10 moles per mole of the alcohol.

15 Claims, 2 Drawing Figures

LIQUID BIODEGRADABLE SURFACTANT AND USE THEREOF

TECHNICAL FIELD

The present invention is directed to liquid biodegradable surfactants and, particularly, certain surfactants having oxyethylene and oxypropylene groups attached to the residue of an alcohol. In addition, the present invention is directed to the use of the liquid biodegradable surfactants. The liquid biodegradable surfactants of the present invention are suitable for use in cold water detergents.

BACKGROUND ART

Surfactants are used in a variety of detergents throughout industry and in the home in applications where it is desirable to reduce the surface and interfacial tension of water so that it will easily wet the surfaces of solid materials and promote cleaning. In order to meet the many demands placed upon these materials by reason of their varied applications and uses, detergents are produced in various forms and have many different combinations of properties. For instance, detergents may be solids or liquids; they may be anionic, cationic, non-ionic, or amphoteric; they may vary in their degree of water solubility; and they may vary considerably in their resistance to degradation by bacterial attack.

Non-ionic liquid surfactants have found particular application for use in aqueous liquid heavy-duty clothes washing compositions and powdered compositions for washing clothes.

In recent years a number of changes have occurred with respect to the requirements of surfactants for detergent compositions. For instance, the temperature at which clothes are washed has significantly decreased over the years in view of the concern for energy conservation. For instance, some twenty to twenty-five years ago in the United States clothes were washed in temperatures of about 140° F. to about 160° F. However, today, the highest temperatures used for washing clothes in the United States is about 120° F. In particular, hot water washing is usually considered to be about 100° F. to about 120° F., warm water washing is usually at about 75° F. to 90° F., and cold water washing is from about room temperature to about 75° F. This significant change in the temperature of the water used in washing clothes has led to the development of the so-called "cold-water" detergents. These detergents are either powders or liquids. The more successful, heavy-duty, liquid detergents generally contain about 30% to about 40% total surfactants being a combination of non-ionic and anionic types. In addition, such commercially successful, heavy-duty, liquid detergents usually contain a "coupling" solvent, such as ethanol or propylene glycol.

The surfactants employed, besides requiring a high degree of detergency for today's detergent market, must include a number of other important characteristics. For instance, the material must be substantially completely degradable by the action of microorganisms in a relatively short period of time. Also, it is desirable that the heavy-duty, liquid detergent compositions be clear and uniform at room temperature and remain so for relatively long periods of time. In particular, the heavy-duty, liquid detergent compositions should, desirably, remain clear and fluid at temperatures of about 50° F. or even lower (e.g.-less than about 40° F.). In addition, such compositions should return to their original form of clarity and appearance, in the event of such cooling or freezing, simply by standing at room temperature without agitation or mixing. This latter property is referred to as "freeze-thaw stability".

Among the more widely used commercial, non-ionic surfactants are the ethylene oxide adducts of $C_{12-15}$ alcohols containing about 60% to 70% ethylene oxide. However, these adducts are from petroleum feed-stocks and have, over the last few years, been subject to significant price increases.

Accordingly, it would be desirable to provide non-ionic surfactants possessing the unique combination of properties which would render such suitable for use in cold-water detergents and which would provide an alternative to the petroleum derived materials.

SUMMARY OF THE INVENTION

The present invention is concerned with liquid biodegradable surfactants. The liquid biodegradable surfactants of the present invention have oxyethylene and oxypropylene groups attached to the residue of an alcohol at the site of the active hydrogen group of the alcohol. The alcohol has 10–22 carbon atoms. The molar ratio of oxyethylene groups to oxypropylene groups is at least 4:1 and the total moles of oxyethylene and oxypropylene groups are about 9–10 moles per mole of the alcohol. In addition, the present invention is concerned with the use of these surfactants in detergents and, particularly, in cold water liquid detergents.

BEST AND VARIOUS MODES FOR CARRYING OUT INVENTION

Figure 1:
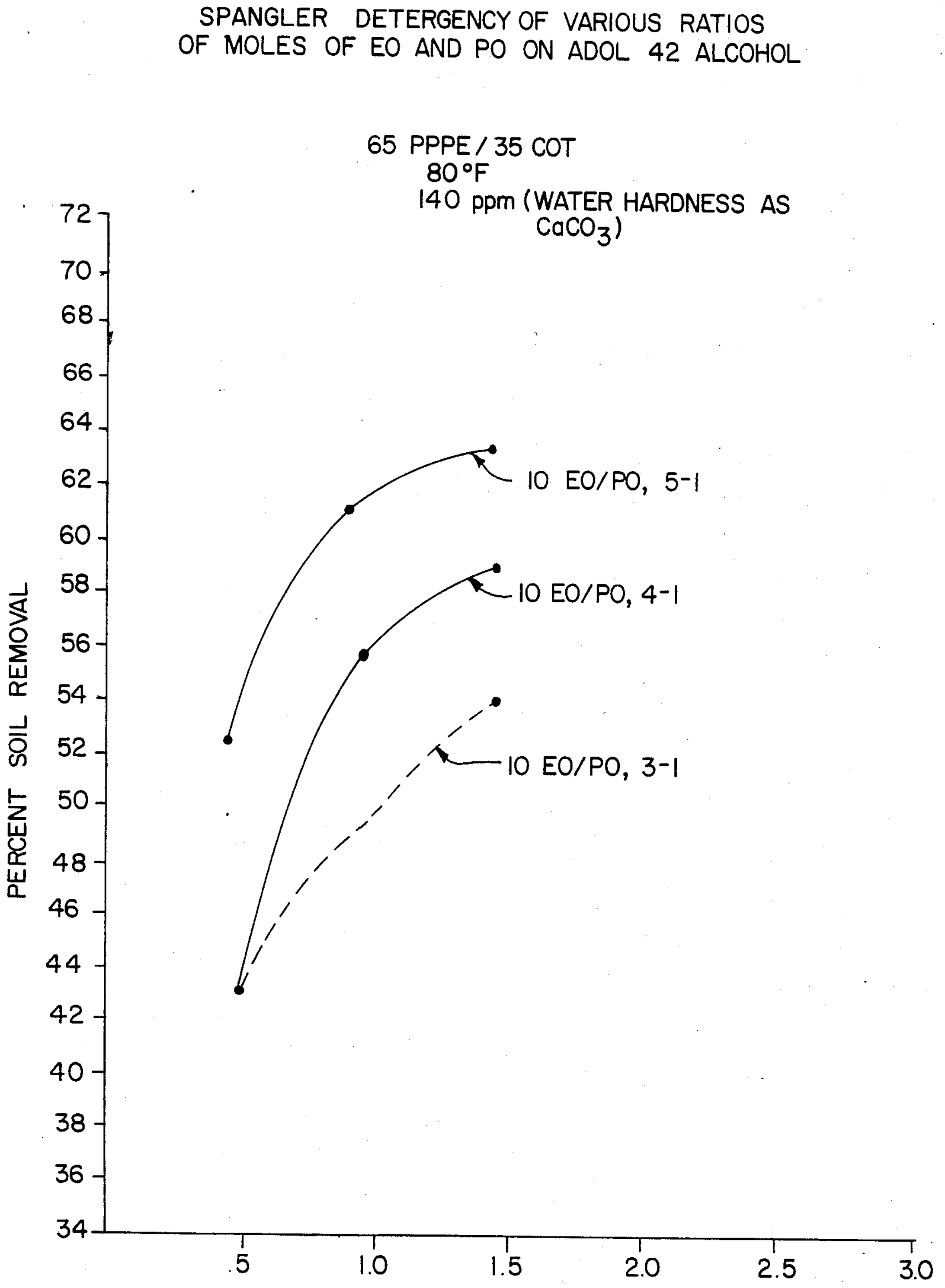
FIG. 1 shows the effect of different ethylene oxide/-propylene oxide ratios upon detergency as tested on polyester/cotton blend fabrics.

The present invention is concerned with liquid biodegradable surfactant and use thereof. In particular, the liquid biodegradable surfactants of the present invention have oxyethylene and oxypropylene groups attached to the residue of an alcohol from the removal of the hydroxylic hydrogen of the alcohol.

The molar ratio of the oxyethylene groups to the oxypropylene groups must be at least 4:1, preferably at least 5:1, and more preferably, about 5:1 to about 10:1, and most preferred, about 5:1 to about 7:1.

In addition, it is essential in the practice of the present invention that the total moles of oxyethylene and oxypropylene groups be about 9 to 10 moles and preferably about 9 moles per mole of the alcohol.

The above parameters with respect to the ratio of oxyethylene groups to oxypropylene groups and the total moles of oxyethylene and oxypropylene groups are necessary in order to obtain a surfactant which is liquid, has good detergency characteristics even in cold water, is clear at normal room temperatures, and has good freeze/thaw stability characteristics when used as components of liquid detergents. Deviating from the above parameters results in significant decrease in these critical properties. In fact, surfactants have been described which differ from the present invention in at least one of the parameters of total moles of oxyethylene and oxypropylene groups, and ratio of oxyethylene to oxypropylene groups and do not possess the essential properties of the materials of the present invention. For instance, U.S. Pat. Nos. 3,382,285 and 3,507,798 to Egan require a total of oxyalkylene units of 12–20 as contrasted to the maximum of only 10 permitted by the present invention. The broad range of oxyethylene units to oxypropylene units disclosed in said patents is 2:1 to 4.5:1, and preferably 2:1 to 3.5:1. In addition, U.S. Ser. No. 414,455, filed Nov. 27, 1964, the parent application to U.S. Pat. No. 3,382,258 and now abandoned, suggests biodegradable surfactants wherein the ratio of oxyethylene groups to oxypropylene groups can range from 1:1 to 10:1, preferably 2:1 to 5:1, and most preferably, 3:1. The total moles of oxyethylene and oxypropylene groups per mole of alcohol are 8 to 20 and preferably 12 to 18. No examples are disclosed in any of the above materials containing both the ratio of oxyethylene to oxypropylene groups and total moles of such, as required by the present invention. Moreover, there is no suggestion therein that by employing the ratios required by the present invention that the properties with respect to liquidity, cold water detergency, freeze/thaw stability, and clarity at room temperature, would be achieved. This is particularly so since none of the above patents and application even discuss cold water detergency and freeze/thaw stability. This is not unexpected since the use of cold water for washing clothes has only come into wide use over the last few years.

In addition, U.S. Pat. No. 3,770,701 to Cenker, et al., which was involved in Interference 96880 with U.S. Pat. No. 3,382,285, suggests surfactants from saturated alcohols. No example in this patent suggests both the ratio of oxyethylene and oxypropylene groups and total moles of polyoxyalkylene groups, as required by the present invention. For instance, see example III (see Table I) whereby the total moles of polyalkylene groups per mole of alcohol is about 11, as contrasted to about 9–10, as required by the present invention. The ratio of oxyethylene to oxypropylene groups is about 8. Moreover, this patent does not discuss freeze/thaw stability, and does not discuss cold water detergency.

The base material of the condensation product of the present invention is a higher aliphatic monohydric primary alcohol, preferably a fatty alcohol having an average of 12–20 carbon atoms per molecule. The alcohols are preferably straight-chain and preferably contain a significant amount of unsaturation. Examples of some commercially available alcohols which can be employed in the preparation of the polyoxyalkylene products of the present invention are Adol 42, Adol 63, and Conoco 1618-S. The base material is preferably a mixture of alcohols having 14–18 carbon atoms per molecule. Adol 63 and Adol 42 are mixtures of alcohols derived from tallow. Adol 63 has a typical composition of about 5% by weight of $C_{14}$ alcohol, about 30% by weight of $C_{16}$ alcohol, and about 65% by weight of $C_{18}$ alcohol. Adol 42 has a typical composition of about 5% by weight of $C_{14}$ alcohol, about 23% by weight of saturated $C_{16}$ alcohol, about 4% by weight of monoethylenically unsaturated $C_{16}$ alcohol, about 23% by weight of saturated $C_{18}$ alcohol, about 42% by weight of monoethylenically unsaturated $C_{18}$ alcohol, and about 3% by weight of diethylenically unsaturated $C_{18}$ alcohol. The mixture of tallow derived alcohols can be saturated or more preferably, a mixture of saturated and unsaturated alcohols.

According to the preferred aspects of the present invention, the alcohol used in the preparation of the surfactant has a minimum iodine value (I.V.) of at least about 40. Moreover, according to the preferred aspects of the present invention, the surfactant has a minimum iodine value (I.V.) of at least about 13.8.

The products of the present invention can be prepared by mixing the reactant materials and then heating to an elevated temperature in the reaction vessel and, a small amount of pressure in the presence of catalysts which promote the condensation reaction. In a typical procedure, the alcohol is placed in a vessel and is stirred and heated to a temperature in the range of about 225° F. to about 400° F. The ethylene oxide and propylene oxide are then added simultaneously to the alcohol at a rate which is slow enough to prevent a run-away reaction. It makes no difference whether the oxides are added as a single stream of mixed oxides, whether they are added from two separate streams, or whether they are added alternatively in small, incremental amounts. In preferred aspects of the present invention, the two oxides are added substantially simultaneously; that is, all of one oxide should not be added before any of the other oxide is added. This results in a product having randomly distributed oxyethylene and oxypropylene groups.

Pressure of the reaction may be essentially atmospheric or it may be above atmospheric. Pressure may vary from about atmospheric to about 200 psig.

The reaction times experienced in this process vary inversely with the reaction temperature; that is, at lower temperatures, the reaction times are longer and at higher temperatures, the reaction times are shorter. Typical reaction times may vary from about one and one-half to about three hours. This process is catalyzed by certain ionic, alkaline catalysts, principally strong bases or salts thereof with weak acids. In addition, dilute solutions of the hydroxides may be employed (e.g., potassium hydroxide). The preferred catalysts employed are the sodium, potassium, and quaternary ammonium salts, and hydroxides. The concentration of these catalysts in the reaction mixture generally is from about 0.1% to about 5% by weight of the alcohol reactant.

The products of the present invention can be used in built or non-built detergents, they can be used in liquid or semi-liquid paste, and powder detergent formulations. However, the preferred use of the surfactants of the present invention is in liquid detergent compositions. In non-built detergents, the surfactants of the present invention can be used, per se, as dilute aqueous solutions (e.g., about 5% to about 50% by weight concentration), or can be mixed with about 85% to 95% by weight of a filler, such as sodium sulfate. In built formulations, where the surfactants of the present invention are employed, for example, with conventional alkaline builders, the surfactants of the present invention will generally amount to about 5% to about 20% by weight of the formulation. However, the preferred amount is about 8% to about 15% by weight of the formulation. It has been found that liquid compositions of the present invention can employ up to about 50% by weight of total surfactant. In fact, compositions containing 30% by weight of total surfactant have been employed. Such amounts can be employed without the use of coupling agents or hydrotropes (e.g., ethanol and xylene sulfonate) which have previously been required in order that the prior detergents pass the necessary cloud point tests employed. However, with the surfactants of the present invention, it is not necessary to use such coupling agents.

In built formulations, the conventional components such as foamers (e.g., sodium lauryl sulfate, sodium linear alkyl benzene sulfonates, fatty alcohol sulfates, and ether sulfates and mixtures thereof); foam stabilizers (e.g., fatty alkanol amides and fatty amine oxides); sequestering agents (e.g., sodium tripolyphosphate and trisodium nitrilotriacetate); corrosion inhibitors or anti-tarnish agents (e.g., sodium metasilicate), soil suspending agents (e.g., sodium carboxymethylcellulose), inert fillers (e.g., sodium sulfate), and optical brighteners can be used in their conventional amounts.

Built formulations are especially suitable for heavy-duty clothes cleaning detergent products.

Other formulations in which the surfactants of the present invention can be employed include light-duty, fine fabric detergents, dishwashing liquids and powders, dairy detergents, metal cleaners, paper machine felt cleaners, floor cleaners, automobile washing detergents, textile wetting liquids, steam cleaners, emulsion cleaners, cutting oils, aircraft cleaners, bottle washing cleaners, and detergent sanitizers.

In addition, since the surfactants of the present invention are non-ionic, such can be readily formulated with other types of surface-active agents including non-ionic, anionic, or cationic materials.

The surfactants of the present invention, in addition to the above-discussed combination of properties, have good alkali and acid stability and are soluble in a wide variety of polar and non-polar solvents, which make these materials readily adaptable in a wide variety of formulations. Where desired, the surfactants of the present invention can be conventionally bleached, such as with hydrogen peroxide or to obtain colors of 1− on the Gardner scale. In addition to use as detergents or in detergent formulations, the surfactants of the present invention can also be used as detergents and wetting agents for various substrates, such as wood, ceramic tile, asphalt tile, vinyl tile, metals, glass, and other substrates which can be cleansed.

The following non-limiting examples are presented to further illustrate the present invention:

EXAMPLE 1

A series of tests are carried out in which products produced by condensing alcohols with different proportions of ethylene oxide and propylene oxide are produced and evaluated in detergent formulations. In each instance, except as indicated below, the process for preparing the condensation products is substantially the same and proceeds as follows:

The alcohol (Adol 42) is charged into a vessel and 0.3% by weight of 85% potassium hydroxide, based on the weight of the alcohol, is placed into the vessel;

the vessel is heated to about 220° F. and sparged with nitrogen;

the vessel is placed under a vacuum of about 25–29 inches Hg, and held for about one-half hour at about 220° F.;

the vacuum is broken with nitrogen, and the vessel is heated to about 330° F.;

the ethylene oxide and propylene oxide are introduced as a mixture into the vessel at a temperature of about 330° F. (the condensation reaction is exothermic, causing the reaction temperature to increase);

the reaction is continued at a pressure of about 35–40 psig and a temperature of about 350° F. to about 370° F.;

after the addition of alkylene oxide material is completed, the pressure is reduced to atmospheric and the vessel is cooled to about 200° F.;

a sufficient amount of phosphoric acid is added to neutralize the hydroxide and the contents of the reaction mass are agitated for an additional half hour, following which the vessel is cooled to the desired temperature and the product is filtered.

The resulting condensation products are evaluated in a formulation described hereinbelow at varying concentrations of 0.5, 1, and 1.5 grams of the formulation per liter of wash water. The formulation has the following composition:

| Component | Weight Percent |
|---|---|
| Non-ionic surfactant | 22.5 |
| Sodium dodecyl benzene sulfonate (60% aqueous solution) | 12.5 |
| Triethanol amine | 2.0 |
| Ethanol | 5.0 |
| Potassium chloride | 2.0 |
| Water | 56.0 |

The formulations are evaluated by using such in a standard wash and dry cycle on a standard soiled swatch of material, according to the general operating procedure described in the Terg-o-tometer instruction manual of the U.S. Testing Co., Inc. The reflectance of the swatch before and after washing is measured. The percentage increase in reflectance is a measure of the cleaning efficiency of the composition tested. The wash conditions employed are as follows:

Terg-o-tometer: Six 3×4 inch test swatches of each type in 1000 ml of water. Wash for 10 minutes and rinse 5 minutes at 100 cpm.

Water: hardness (as calcium carbonate); 140 ppm

Temperature: 80° F. wash and rinse

Detergent Concentration: 0.5, 1.0, and 1.5 grams of formulated product per liter of wash water

Test Fabrics and Soils

Fabric: polyester/cotton (65/35).

Soil: Spangler (Sebum and air conditioner dust).

Source: Scientific Services

Fabric: cotton

Soil: Krefeld-woolfat, clay, carbon, and metal oxides

Source: Testfabrics, Inc.

Detergency: Defined as increase in reflectance or of soil removal, R, $$R = \frac{Rw - Rs}{Ro - Rs} \times 100$$

Wherein:

Rw = reflectance reading of the washed swatches

Rs = reflectance reading of the soiled swatches

Ro = reflectance reading of the unsoiled swatches

Figure 2:
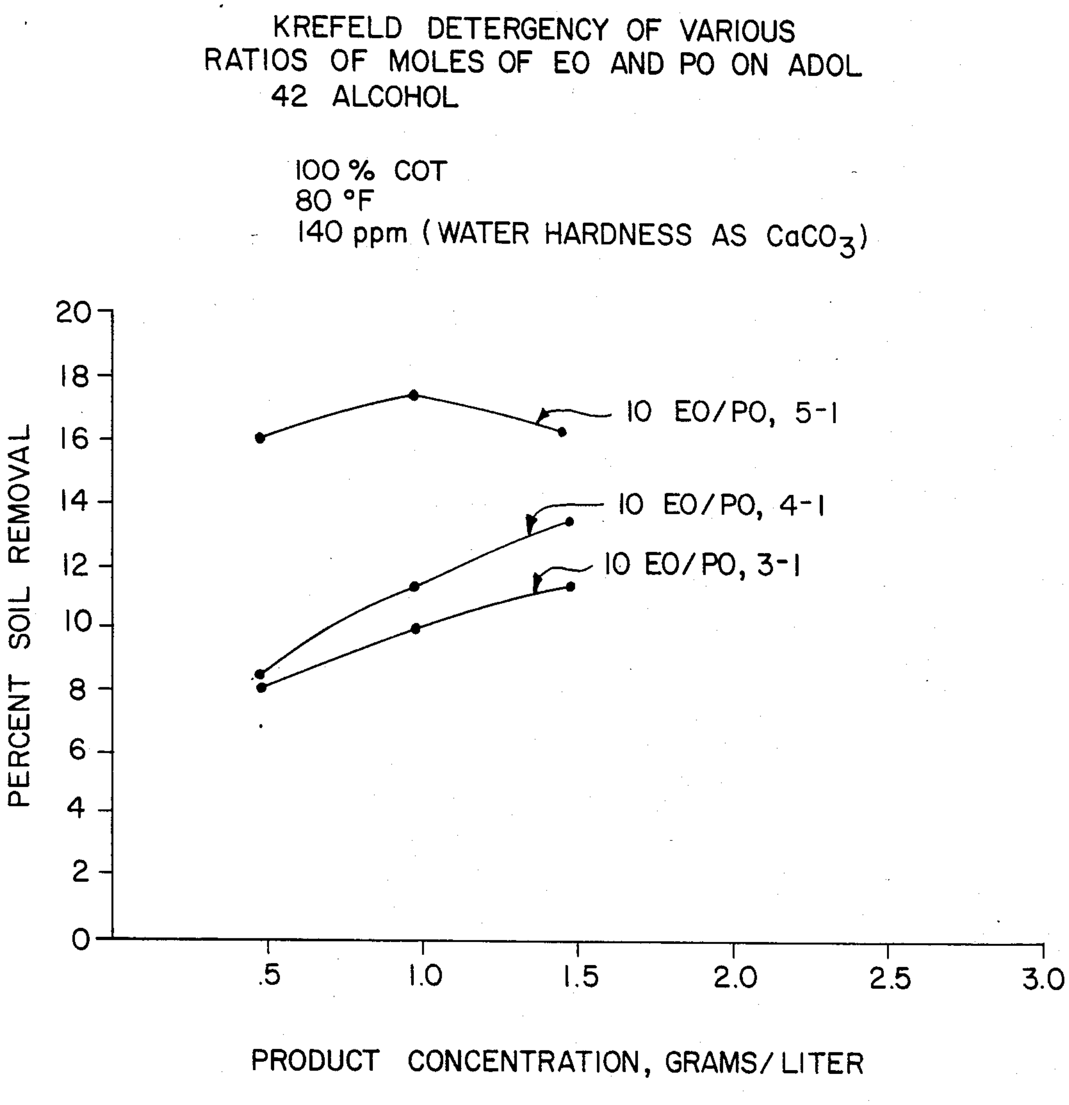
FIG. 2 shows a similar comparison with 100% cotton fabrics.

The results obtained for varying ratios of moles of ethylene oxide and propylene oxide are shown in FIGS. 1 and 2. As apparent from FIGS. 1 and 2, the products of the present invention, wherein the ethylene oxide to propylene oxide is at least 4:1, provide greatly improved detergency characteristics, as compared to products differing only in employing a ratio of ethylene oxide to propylene oxide of 3:1, with the same total moles of alkylene oxide per mole of alcohol. In particular, curve 1 in FIGS. 1 and 2 represents a product of ratio of ethylene oxide to propylene oxide of 5:1 and total moles of alkylene oxide of 10. Curve 2 in said Figures represents total moles of alkylene oxide of 10 and ratio of ethylene oxide to propylene oxide of 4:1. Curve 3 in FIGS. 1 and 2 represents a ratio of ethylene oxide to propylene oxide of 3:1 and total moles of alkylene oxide of 10.

EXAMPLE 2

A composition containing about 22.5% by weight of a non-ionic surfactant pursuant to the present invention from Adol 42 as the alcohol and having a ratio of oxyethylene groups to oxypropylene groups of 5:1 and total moles of oxyethylene and oxypropylene groups of about 9.6 moles per mole of alcohol, about 12.5% by weight of sodium dodecyl benzene sulfonate as a 60% aqueous solution, about 2% by weight of triethanol amine, about 5% by weight of ethanol, 2% by weight of potassium chloride, and about 56.0% by weight of water is obtained. The composition at 81° F. is clear and has a viscosity of about 175 centipoises.

At 40° F. the composition is clear and has a viscosity of about 1800 centipoises. The cloud point of the composition is less than 30° F.

EXAMPLE 3

Example 2 is repeated, except that the non-ionic surfactant has total moles of oxyethylene and oxypropylene groups of about 9.65 moles per mole of alcohol. The composition at 81° F. is clear and has a viscosity of about 170 centipoises. At 40° F. the composition is clear and has a viscosity of about 1375 centipoises. The cloud point of the composition is less than 30° F.

EXAMPLE 4

A composition containing about 22.5% by weight of the same non-ionic surfactant as employed in Example 2, about 12.5% by weight of sodium dodecyl benzene sulfonate as a 60% aqueous solution, about 2% by weight of triethanol amine, and about 63% by weight of water is obtained. The composition at 81° F. is clear and has a viscosity of about 140 centipoises. At 40° F. the composition is clear and has a viscosity of about 195 centipoises. The cloud point of the composition is less than about 32° F.

EXAMPLE 5

Example 4 is repeated, except that the non-ionic surfactant is the same as that employed in Example 3. The composition at 81° F. is clear and has a viscosity of about 130 centipoises. At 40° F. the composition is clear and has a viscosity of about 170 centipoises. The cloud point of the composition is less than about 33° F.

EXAMPLE 6

A composition containing about 37.5% by weight of the same non-ionic surfactant as employed in Example 2, about 20.8% by weight of sodium dodecyl benzene sulfonate as a 60% aqueous solution, about 2% by weight of triethanol amine, about 6% by weight of ethanol, about 1% by weight of potassium chloride, and about 29.7% by weight of water. This composition contains about 50% by weight of active ingredients and is primarily intended to be diluted with water by the consumer to a composition containing about 30% by weight of active ingredients.

The composition at 81° F. is clear and has a viscosity of about 150 centipoises. At 40° F. the composition is cloudy and has a viscosity of about 1700 centipoises. The cloud point of the composition is about 46° F.

EXAMPLE 7

Example 6 is repeated, except that the non-ionic surfactant is the same as that employed in Example 3. The composition at 81° F. is clear and has a viscosity of about 150 centipoises. At 40° F. the composition is cloudy and has a viscosity of about 1600 centipoises. The cloud point of the composition is about 48° F.

The compositions described in the above examples all exhibit freeze-thaw stability. The above examples demonstrate that the surfactants of the present invention provide excellent detergency properties while, at the same time, possessing the physical characteristics crucial for employing such in heavy-duty liquid detergents.

What is claimed is:

1. A liquid biodegradable surfactant having oxyethylene and oxypropylene groups attached in a random distribution to the residue of a primary monohydric alcohol at the site of its active hydrogen group; which alcohol has 10–22 carbon atoms and a minimum iodine value of at least 40, the ratio of oxyethylene groups to oxypropylene groups being at least 4:1, and the total moles of oxyethylene and oxypropylene groups being about 9–10 moles per mole of said alcohol.

2. The surfactant of claim 1 wherein the ratio of oxyethylene groups to oxypropylene groups is at least 5:1.

3. The surfactant of claim 1 wherein the ratio of oxyethylene groups to oxypropylene groups is about 5:1 to about 10:1.

4. The surfactant of claim 1 wherein the ratio of oxyethylene groups to oxypropylene groups is about 5:1 to about 7:1.

5. The surfactant of claim 4 wherein said alcohol is derived from tallow.

6. The surfactant of claim 4 wherein said alcohol has an average of 12–20 carbon atoms per molecule.

7. The surfactant of claim 1 wherein the total moles of oxyethylene and oxypropylene groups is about 9 moles per mole of the alcohol.

8. The surfactant of claim 1 having a minimum iodine value of at least about 13.8.

9. The surfactant of claim 1 wherein said alcohol has an average of 12–20 carbon atoms per molecule.

10. The surfactant of claim 1 wherein the alcohol contains 14 to 18 carbon atoms.

11. The surfactant of claim 1 wherein said alcohol is derived from tallow.

12. The surfactant of claim 1 wherein said alcohol is a straight chain alcohol.

13. A detergent composition containing the surfactant of claim 1 and a diluent.

14. An aqueous detergent composition containing about 5% to about 50% by weight of the surfactant of claim 1.

15. A built detergent formulation containing an alkaline builder and about 5% to about 20% by weight of the surfactant of claim 1.

* * * * *